US009867765B2

(12) United States Patent
Franklin et al.

(10) Patent No.: US 9,867,765 B2
(45) Date of Patent: Jan. 16, 2018

(54) ANTIPERSPIRANT COMPOSITIONS

(71) Applicant: Conopco, Inc., Englewood Cliffs, NJ (US)

(72) Inventors: Kevin Ronald Franklin, Wirral (GB); Philip Christopher Waterfield, Heswall (GB); Karim Mohamed Anwar M Fawzy, Llsburn (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/547,501

(22) Filed: Nov. 19, 2014

(65) Prior Publication Data
US 2016/0136066 A1 May 19, 2016

(51) Int. Cl.
A61K 8/26 (2006.01)
A61Q 15/00 (2006.01)
A61K 8/44 (2006.01)
A61K 8/20 (2006.01)

(52) U.S. Cl.
CPC ............... A61K 8/26 (2013.01); A61K 8/20 (2013.01); A61K 8/44 (2013.01); A61Q 15/00 (2013.01)

(58) Field of Classification Search
None
See application file for complete search history.

(56) References Cited

U.S. PATENT DOCUMENTS

| | | | |
|---|---|---|---|
| 4,359,456 A | 11/1982 | Gosling | |
| 4,435,382 A * | 3/1984 | Shin | A61K 8/26 424/66 |
| 5,955,065 A | 9/1999 | Thong | |
| 6,042,816 A | 3/2000 | Shen | |
| 6,261,543 B1 | 7/2001 | Fletcher et al. | |
| 6,911,195 B2 | 6/2005 | Vu | |
| 6,942,850 B2 | 9/2005 | Coe | |
| 7,087,220 B2 | 8/2006 | Li | |
| 7,704,531 B2 * | 4/2010 | Tang | A61K 8/19 424/400 |
| 2003/0215399 A1 | 11/2003 | Smith | |
| 2004/0115147 A1 | 6/2004 | Vu | |
| 2005/0163737 A1 | 7/2005 | Lemoine | |
| 2006/0222612 A1 | 10/2006 | Ni | |
| 2007/0020211 A1 | 1/2007 | Li | |
| 2007/0196303 A1 * | 8/2007 | Li | A61K 8/26 424/68 |
| 2007/0286830 A1 | 12/2007 | Li | |
| 2008/0131354 A1 | 6/2008 | Li | |
| 2008/0241089 A1 | 10/2008 | Banowski et al. | |
| 2010/0303749 A1 | 12/2010 | Pan | |
| 2011/0038823 A1 | 2/2011 | Phipps | |
| 2011/0038902 A1 | 2/2011 | Phipps et al. | |
| 2011/0274637 A1 | 11/2011 | Milardovic | |
| 2014/0178321 A1 | 6/2014 | Banowski | |
| 2014/0301963 A1 * | 10/2014 | Claas | A61K 8/26 424/68 |

FOREIGN PATENT DOCUMENTS

| | | |
|---|---|---|
| CN | 1323191 | 11/2001 |
| EP | 0308937 | 3/1989 |
| EP | 0405598 | 1/1991 |
| EP | 1104282 | 6/2001 |
| GB | 2113116 | 8/1983 |
| WO | WO0010512 | 3/2000 |
| WO | WO2009044381 | 4/2009 |
| WO | WO2009075678 | 6/2009 |
| WO | WO2009076592 | 6/2009 |
| WO | WO2008063188 | 9/2010 |
| WO | WO2011016807 | 2/2011 |
| WO | WO2012021356 | 2/2012 |
| WO | WO2012060817 | 5/2012 |
| WO | WO2012061280 | 5/2012 |
| WO | WO2012148480 | 11/2012 |
| WO | WO2012148481 | 11/2012 |
| WO | WO2013158077 | 10/2013 |
| WO | WO2014187684 | 11/2014 |
| WO | WO2014187685 | 11/2014 |

OTHER PUBLICATIONS

Search Report & Written Opinion in PCTEP2015074528 dated Jan. 20, 2016.
Search Report & Written Opinion in PCTEP2015074529 dated Dec. 21, 2015.
Search Report in PCTEP2014059582, Oct. 6, 2014, p. 1 to p. 4.
Search Report in PCTEP2014059583, Oct. 6, 2014, p. 5 to p. 8.
Search Report in PCTEP2014060306, Oct. 6, 2014, p. 9 to p. 12.
Written Opinion in PCTEP2014059582, Oct. 6, 2014, p. 13 to p. 18.
Written Opinion in PCTEP2014059583, Oct. 6, 2014, p. 19 to p. 24.
Written Opinion in PCTEP2014060306, Oct. 6, 2014, p. 25 to p. 30.
IPRP2 in PCTEP2014059583 dated Sep. 11, 2015. pp. 1 to 13.
IPRP2 in PCTEP2014060306 dated Sep. 16, 2015. pp. 14 to 27.
Laden, Antiperspirants and Deodorants 1999 2nd Edition pp. 96-97. pp. 28 to 29.
Search Report in EP13168417 dated Oct. 31, 2013. pp. 1 to 2.
Search Report in EP13168418 dated Oct. 31, 2013. pp. 3 to 4.
Search Report in EP14190530 dated Feb. 12, 2015. pp. 5 to 6.
Search Report in EP14190531 dated May 8, 2015. pp. 7 to 8.
Search Report in EP14193902 dated May 6, 2015. pp. 9 to 10.
Written Opinion 2 in PCTEP201406030 dated May 8, 2015. pp. 1 to 9.
Written Opinion in EP13168417 dated Oct. 31, 2013. pp. 10 to 13.
Written Opinion in EP13168418 dated Oct. 31, 2013. pp. 14 to 17.
Written Opinion in EP14190530 dated Feb. 12, 2015. pp. 18 to 20.
Written Opinion in EP14190531 dated May 8, 2015. pp. 21 to 23.
Written Opinion in EP14193902 dated May 6, 2015. pp. 14 to 24.
Search Report & Written Opinion in PCTEP2015076365, Feb. 11, 2016.
Pluronic(R) F-127, Newdruginfo.com, Jun. 7, 2016, 1 page.
Search Report & Written Opinion in PCTEP2016080034, Feb. 9, 2017.

(Continued)

Primary Examiner — Melissa Fisher
(74) Attorney, Agent, or Firm — Karen E. Klumas

(57) ABSTRACT

An aqueous composition comprising an aluminum sesquichlorohydrate salt, water soluble calcium salt, and amino acid, wherein the molar ratio of water soluble calcium salt to aluminum is at least 1:40 and the molar ratio of amino acid to aluminum is at least 1:20 and methods for making such compositions having enhanced antiperspirancy performance.

7 Claims, No Drawings

(56) References Cited

OTHER PUBLICATIONS

Co-pending U.S. Appl. No. 14/889,866, Karim Mohamed Anwar M Fawz, filed Nov. 9, 2015.
Co-pending U.S. Appl. No. 14/889,874, Karim Mohamed Anwar M Fawz, filed Nov. 9, 2015.
Co-pending U.S. Appl. No. 14/889,863, Karim Mohamed Anwar M Fawz, filed Nov. 9, 2015.
Co-pending U.S. Appl. No. 15/520,652, Duncan Alexander Court, filed Apr. 20, 2017.
Co-pending U.S. Appl. No. 15/520,615, Duncan Alexander Court, filed Apr. 20, 2017.

* cited by examiner

ANTIPERSPIRANT COMPOSITIONS

The present invention is concerned with antiperspirant compositions and with methods of making the same. It is particularly concerned with the compositions comprising basic aluminium chloride (herein BAC) antiperspirant actives and their manufacture.

The compositions of the present invention may be used as antiperspirant compositions and/or may be used in the manufacture of high efficacy antiperspirant compositions. Using the processes described herein, particularly effective or "activated" BAC compositions may be prepared.

Certain activated BAC active s are commercially available and their preparation and use are disclosed in numerous publications.

Traditionally, activated BAC samples have been prepared by prolonged heating of BAC solutions followed by spray drying; see, for example, U.S. Pat. No. 4,359,456 (Gosling). The samples prepared by this method needed to be formulated into essentially anhydrous compositions in order for the antiperspirant to maintain its high activity.

Activated BAC samples have also been prepared using water soluble calcium acids, particularly with a further adjunct such as an amino acid, hydroxyl acid, or betaine. Some of these samples could be formulated into aqueous compositions without the antiperspirant losing all of its enhanced activity.

EP 1,104,282 (Gillette) discloses a means of producing activated BAC samples using a water soluble calcium salt and an amino acid or a hydroxy acid.

U.S. Pat. No. 6,911,195 (Gillette) discloses water-in-oil emulsion gels comprising aluminium-zirconium antiperspirant salts activated using calcium ions.

U.S. Pat. No. 5,955,065 (Gillette) discloses anhydrous suspension formulations comprising particulate BAC and aluminium-zirconium antiperspirant salts activated using calcium ions.

U.S. Pat. No. 6,942,850 (Gillette) discloses aqueous alcoholic composition comprising aluminium-zirconium antiperspirant salts activated using calcium ions.

WO 2009/044381 (P&G) discloses water-in-oil emulsion sticks comprising BAC and aluminium-zirconium antiperspirant salts activated using calcium ions.

U.S. Pat. No. 7,704,531 (Colgate) discloses compositions comprising an active system made from combining an aluminium or aluminium-zirconium salt, a calcium salt, and a betaine.

US 2011/0038823 (Dial/Henkel) discloses water-in-oil emulsion sticks comprising an antiperspirant active prepared by combining BAC, calcium chloride and glycine.

US 2007/196303, US 2007/0020211, WO 2008/063188, US 2008/0131354 and U.S. Pat. No. 7,087,220 (Summit and Reheis) each describe methods of making calcium-activated antiperspirant salts.

WO 2009/075678, WO 2009/076592, WO 2011/016807, WO 2012/060817, WO 2012/061280, WO 2012/148480 and WO 2012/148481 (Colgate) disclose the manufacture of activated antiperspirant salts by neutralisation of aluminium chloride with calcium hydroxide in the presence of glycine.

The present invention is particularly concerned with BAC compositions comprising aluminium sesquichlorohydrate (herein ASCH) of chemical formula $Al_2(OH)_{4.4}Cl_{1.6}$ to $Al_2(OH)_{4.9}Cl_{1.1}$. This material is commercially available, but its formulation and use described herein are new and deliver unexpected benefits.

In a first aspect of the present invention, there is provided an aqueous composition comprising an aluminium sesquichlorohydrate salt, water soluble calcium salt, and amino acid, wherein the aluminium sesquichlorohydrate salt is of formula $Al_2(OH)_{4.4}Cl_{1.6}$ to $Al_2(OH)_{4.9}Cl_{1.1}$ and the molar ratio of water soluble calcium salt to aluminium is at least 1:40 and the molar ratio of amino acid to aluminium is at least 1:20.

In a method of manufacture of an aqueous antiperspirant composition comprising the steps of: (i) mixing aluminium sesquichlorohydrate salt, water soluble calcium salt, amino acid, and water, (ii) heating the mixture to a temperature of at least 65° C., and (iii) cooling the mixture to ambient temperature, wherein the aluminium sesquichlorohydrate salt used is of formula $Al_2(OH)_{4.4}Cl_{1.6}$ to $Al_2(OH)_{4.9}Cl_{1.1}$ and the molar ratio of water soluble calcium salt to aluminium is at least 1:40 and the molar ratio of amino acid to aluminium is at least 1:20.

In a third aspect of the present invention, there is provided a method of attaining an antiperspirant benefit comprising the topical application to the surface of the human body of a composition according to the first aspect of the invention, especially when manufactured in accordance with the second aspect of the invention.

Aqueous compositions according to the first aspect of the invention may be used in the method of manufacture according to the second aspect of the invention. Aqueous compositions resulting from such a process have enhanced antiperspirancy performance.

In a fourth aspect of the present invention, there is provided a process for improving the antiperspirant activity of a aluminium sesquichlorohydrate salt of formula $Al_2(OH)_{4.4}Cl_{1.6}$ to $Al_2(OH)_{4.9}Cl_{1.1}$, said process comprising the steps of (i) mixing the basic aluminium chloride salt, water soluble calcium salt, amino acid, and water, (ii) heating the mixture to a temperature of at least 65° C., and (iii) cooling the mixture to ambient temperature, wherein the molar ratio of water soluble calcium salt to aluminium is at least 1:40 and the molar ratio of amino acid to aluminium is at least 1:20.

Herein, the "activation mixture" refers to the mixture of aluminium sesquichlorohydrate salt of formula $Al_2(OH)_{4.4}Cl_{1.6}$ to $Al_2(OH)_{4.9}Cl_{1.1}$, water soluble calcium salt, amino acid, and water.

The choice of BAC salt used is critical to the success of the present invention. We have found that surprisingly good results are found on using BAC salts commonly referred to as aluminium sesquichlorohydrate (herein ASCH) having the chemical formula $Al_2(OH)_{4.4}Cl_{1.6}$ to $Al_2(OH)_{4.9}Cl_{1.1}$. Most commercial ASCH samples are of chemical formula $Al_2(OH)_{4.7}Cl_{1.3}$ to $Al_2(OH)_{4.9}Cl_{1.1}$ and it is preferred to use BAC salts of this formula.

The surprisingly good results referred to in the above paragraph include surprisingly good antiperspirancy performance. In addition, compositions prepared according to the present invention have remarkable storage stability, maintaining their good performance for many months.

The aluminium sesquichlorohydrate salt used in the present invention has aluminium to chloride molar ratio of from 1.25:1 to 1.82:1 and preferably 1.54:1 to 1.82:1.

In order for the antiperspirant to become activated, it is important to have sufficient calcium present relative to the amount of aluminium present. The molar ratio of calcium to aluminium is at least 1:40, preferably at least 1:30 and more preferably at least 1:20. It is not advantageous to have the calcium concentration in excess of the aluminium concentration, indeed it is preferred that the calcium concentration is no more than half that of the aluminium concentration and more preferred that it is no more than a fifth of said concentration. For the preferred molar ratio of calcium to aluminium of at least 1:20, it is independently preferred that this ratio is no greater than 1:2 and more preferred that it is no greater than 1:5.

In particularly preferred embodiments, the molar ratio of calcium to aluminium is at least 1:15 and preferably no greater than 1:5 and in especially preferred embodiments it is at least 1:10 and preferably no greater than 1:5.

A preferred water soluble calcium salt for use in the present invention is calcium chloride.

Herein, references to molar amounts and ratios of "aluminium" are calculated on the basis of mono-nuclear aluminium, but include aluminium present in poly-nuclear species; indeed, most of the aluminium in the salts of relevance is present in poly-nuclear species.

In order for the antiperspirant to become activated, it is important to have sufficient amino acid present relative to the amount of aluminium present. The molar ratio of amino acid to aluminium is at least 1:20, preferably at least 1:10 and most preferably at least 1:5. It is not advantageous to have the amino acid concentration in excess of the aluminium concentration; hence, the molar amino acid to aluminium is preferably from 1:20 to 1:1, more preferably from 1:10 to 1:1 and most preferably from 1:5 to 1:1.

In particularly preferred embodiments, the molar ratio of amino acid to aluminium is at least 1:4 and preferably no greater than 1:1 and in especially preferred embodiments it is at least 1:3 and preferably no greater than 1:1.

The presence of both calcium and amino acid is essential for the success of the present invention. In preferred embodiments, the molar ratio of calcium to aluminium is at least 1:20 and the molar ratio of amino acid to aluminium is at least 1:10. In particularly preferred embodiments the molar ratio of calcium to aluminium is from 1:20 to 1:5 and the molar ratio of amino acid to aluminium is from 1:10 to 1:1.

In certain especially preferred embodiments, the molar ratio of calcium to aluminium is from 1:15 to 1:5 and the molar ratio of amino acid to aluminium is from 1:4 to 1:1. In these especially preferred embodiments, exemplary performance in is obtained when the molar ratio of calcium to aluminium is from 1:10 to 1:5 and the molar ratio of amino acid to aluminium is from 1:3 to 1:1.

The above indicated preferences for calcium to aluminium molar ratio and/or amino acid to aluminium molar ratio lead to compositions of higher Band III content (vide infra) and, in general, higher antiperspirancy performance. It will be noted that higher Band III content is generally indicative of higher antiperspirancy performance.

It is noteworthy that an amino acid must be used in order to activate the antiperspirant salt. The combination of a water soluble calcium salt and a hydroxy acid, as disclosed in EP 1,104,282 (Gillette), was found to be unsuccessful (vide infra). Preferred amino acids for use in the present invention are glycine, alanine, valine and proline. A particularly preferred amino acid for use in the present invention is glycine.

The activation process generally produces a mixture of aluminium species having a relatively high content of what is commonly termed Band III material, as determined by SEC (Size Exclusion Chromatography) analysis. The SEC technique employed is well known in the art and is described in further detail in U.S. Pat. No. 4,359,456 (Gosling). The SEC band commonly referred to as Band III is designated as "Peak 4" in EP 1,104,282 B1 by Gillette.

Herein, "Band III content" refers to the integrated area in the Band III region of the SEC chromatograph relative to the total integrated area in all of the regions corresponding to aluminium species; that is to say, Bands I, II, III, and IV.

In particular embodiments of the invention, compositions according to the invention intended for use as antiperspirant compositions preferably have a Band III content of at least 40%, more preferably at least 50% and most preferably at least 60%.

In the activation process and method of manufacture described herein, it is preferred that the activation mixture is heated for sufficient time for the Band III content of the aluminium species to become at least 40%, more preferably at least 50% and most preferably at least 60%.

In the activation process and method of manufacture described herein, the activation mixture is heated to at least 65° C., preferably to at least 75° C., and more preferably to at least 85° C.

The processes described herein produce an aqueous solution of an activated antiperspirant salt. It will be realised, however, that such solutions may be dried by techniques known in the art, notably spray drying, to give a dried antiperspirant salt. Such dried antiperspirant salts may be used in a variety of compositions, including aerosols, sticks and soft solids. Such compositions are also to be considered antiperspirant compositions according to the invention. It will be realised that such compositions may be essentially anhydrous, having less than 1% by weight of free water or may be anhydrous, having less than 0.1% by weight of free water.

Herein, "free water" excludes any water of hydration associated with the antiperspirant salt or other component added to a particular composition, but includes all other water present.

Herein, compositions according to the invention intended for use as antiperspirant compositions are termed "antiperspirant compositions".

Other components may also be including in antiperspirant compositions according to the invention.

Herein, amounts and concentrations of ingredients are percentages by weight of the total composition, unless otherwise indicated and ratios are ratios by weight.

A preferred additional component of compositions of the invention is an oil.

Herein, the terms "oil" and signifies a water-insoluble organic material that is liquid at 20° C. Any material having a solubility of less than 0.1 g/100 g at 20° C. is considered to be insoluble.

Herein "aqueous compositions" are compositions having a continuous phase that is predominately water; that is to say, greater than 50% water.

A preferred oil for use in accordance with the present invention is a fragrance oil, sometimes alternatively called a perfume oil. The fragrance oil may comprise a single fragrance or component more commonly a plurality of fragrance components. Herein, fragrance oils impart an odour, preferably a pleasant odour, to the composition. Preferably, the fragrance oil imparts a pleasant odour to the surface of the human body the composition is applied to the same.

The amount of fragrance oil in the composition is commonly up to 3% advantageously is at least 0.5% and particularly from 0.8% to 2%.

The total amount of oil in the composition is preferably from 0.1 to 20%, more preferably from 0.5 to 10%, and most preferably at from 2 to 8% by weight of the total composition. In certain preferred embodiments, particularly those also comprising an aluminium and/or zirconium containing antiperspirant active, the oil is present at greater than 2.5% and less than 6% by weight of the total composition.

In certain embodiments, it is preferred to include an oil, other than a fragrance oil, that has a relatively low viscosity, by which is meant less 250 cS (mm$^2$·s$^{-1}$). Such oils can improve the sensory properties of the composition on application and can lead to other benefits such as emolliency.

Suitable oils can be selected from alkyl ether oils having a boiling point of above 100° C. and especially above 150° C., including polyalkyleneglycol alkyl ethers. Such ethers desirably comprise between 10 and 20 ethylene glycol or propylene glycol units and the alkyl group commonly contains from 4 to 20 carbon atoms. The preferred ether oils include polypropylene glycol alkyl ethers such as PPG-14-butylether and PPG-15-stearyl ether.

Suitable oils can include one or more triglyceride oils. The triglyceride oils commonly comprise the alkyl residues of aliphatic $C_7$ to $C_{20}$ alcohols, the total number of carbon atoms being selected in conjunction with the extent of olefinic unsaturation and/or branching to enable the triglyceride to be liquid at 20° C. One example is jojoba oil. Particularly preferably, in the triglyceride oil the alkyl residues are linear $C_{18}$ groups having one, two or three olefinic degrees of unsaturation, two or three being optionally conjugated, many of which are extractable from plants (or their synthetic analogues), including triglycerides of oleic acid, linoleic acid, conjugated linoleic acids, linolenic acid, petroselenic acid, ricinoleic acid, linolenelaidic acid, trans 7-octadecenoic acid, parinaric acid, pinolenic acid, punicic acid, petroselenic acid and stearidonic acid.

Suitable oils can include those derived from unsaturated $C_{18}$ acids, including coriander seed oil, *impatiens balsimina* seed oil, *parinarium laurinarium* kernel fat oil, *sabastiana brasilinensis* seed oil, dehydrated castor seed oil, borage seed oil, evening primrose oil, *aquilegia vulgaris* oil, sunflower (seed) oil and safflower oil. Other suitable oils are obtainable from hemp, and maize corn oil. An especially preferred oil by virtue of its characteristics is sunflower (seed) oil.

Further suitable oils, that can also be emollient oils, comprise alkyl or alkyl-aryl ester oils having a boiling point of above 150° C. (and a melting point of below 20° C.). Such ester oils include oils containing one or two alkyl groups of 12 to 24 carbon atoms length, including isopropyl myristate, isopropyl palmitate and myristyl palmitate. Other non-volatile ester oils include alkyl or aryl benzoates such $C_{12-15}$ alkyl benzoate, for example Finsolv TN™ or Finsolv Sun™.

A further class of suitable oils comprises non-volatile dimethicones, often comprising phenyl or diphenylene substitution, for example Dow Corning 200 350 cps or Dow Corning 556.

A preferred component in many antiperspirant compositions, particularly aqueous antiperspirant compositions, according to the invention is an emulsifier. Emulsifiers are particularly advantageous in aqueous systems additionally comprising fragrance oil and/or other oil.

Preferred compositions according to the invention are oil-in-water emulsions comprising an emulsifier, such compositions giving especially effective antiperspirancy, especially when the molar ratio of calcium to aluminium and/or amino acid to aluminium is within the preferred ranges indicated above (vide supra).

It is preferred that emulsifiers used in aqueous antiperspirant compositions of the present invention form a lamellar phase emulsifier system in the composition. Such systems may be readily identified by means of optical microscopy. Such systems lead to good emulsion stability in compositions according to the invention.

It is preferred that aqueous antiperspirant compositions of the present invention comprise a non-ionic emulsifier system. Such an emulsifier system conveniently has a mean HLB value in the region of from about 5 to about 12 and particularly from 6 to about 10. In the preferred embodiments referred to in the paragraph immediately above, an especially desired mean HLB value is from 6 to 9. Such a mean HLB value can be provided by selecting an emulsifier having such an HLB value, or more preferably by employing a combination of at least two emulsifiers, a first (lower) HLB emulsifier having an HLB value in the range of from 2 to 6.5, such as in particular from 4 to 6 and a second (higher) HLB emulsifier having an HLB value in the range of from about 6.5 to 18 and especially from about 12 to about 18. When a combination of emulsifiers is employed, the average HLB value can be calculated as a weight average of the HLB values of the constituent emulsifiers.

Lamellar phase emulsifier systems preferably comprise two non-ionic surfactants, optionally selected as suggested in the paragraph immediately above. In a particular embodiment a first emulsifier is a fatty alcohol, such as cetyl and/or stearyl alcohol and a second emulsifier is much more hydrophilic, having a HLB of from about 6.5 to 18 and especially from about 12 to about 18.

An especially desirable range of emulsifiers comprises a hydrophilic moiety provided by a polyalkylene oxide (polyglycol), and a hydrophobic moiety provided by an aliphatic hydrocarbon, preferably containing at least 10 carbons and commonly linear. The hydrophobic and hydrophilic moieties can be linked via an ester or ether linkage, possibly via an intermediate polyol such as glycerol. A preferred range of emulsifiers comprises polyethylene glycol ethers.

Preferably the hydrophobic aliphatic substituent contains at least 12 carbons, and is derivable from lauryl, palmityl, cetyl, stearyl, and behenyl alcohol, and especially cetyl, stearyl or a mixture of cetyl and stearyl alcohols or from the corresponding carboxylic acids.

The polyalkylene oxide is often selected from polyethylene oxide and polypropylene oxide or a copolymer of ethylene oxide and especially comprises a polyethylene oxide. The number of alkylene oxide and especially of ethoxylate units within suitable emulsifiers is often selected within the range of from 2 to 100. Emulsifiers with a mean number of ethoxylate units in the region of 2 can provide a lower HLB value of below 6.5 and those having at least 4 such units provide a higher HLB value of above 6.5 and especially those containing at least 10 ethoxylate units which provide an HLB value of above 10. A preferred combination comprises a mixture of an ethoxylate containing 2 units and one containing from 10 to 40 units, such as from 15 to 30 or desirably from 20 to 25. Particularly conveniently, the combination of emulsifiers comprises steareth-2 and a selection from steareth-15 to steareth-30.

It is desirable to employ a mixture of ethoxylated alcohol emulsifiers in a weight ratio of emulsifier having a lower HLB value of less than 6.5 to emulsifier having a higher HLB value of greater than 8 of from 2:1 to 6:1 and particularly from 4:1 to 6:1.

The total proportion of emulsifiers in the composition is usually at least 1% and particularly at least 2% by weight. Commonly, the emulsifiers are not present at above 10%, often not more than 7% by weight and in many preferred embodiments up to 6% by weight. An especially desirable concentration range for the emulsifiers is from 2.5 to 5% by weight.

Other components that may be present include short chain ($C_2$-$C_4$) alcohols and especially polyols such glycerol, ethylene glycol, propylene glycol and polymers thereof, in particular poly(ethylene glycol) and poly(propylene glycol). Poly(ethylene glycol) of average molecular weight 200 to 600 is a preferred component. Such components may add to the sensory properties of the composition and, when included, are typically present at from 0.5 to 10% of the total composition.

The aqueous compositions of the present invention are very suitable for dispensing via a roll-on dispenser, for example any upright dispenser such as described in EP1175165 or an invert dispenser such as described in U.S. Pat. No. 6,511,243 or WO05/007377. Invert indicates that the dispenser stands stably with its dispensing ball below the formulation reservoir. In using such dispensers, the composition is applied by rolling the ball of the dispenser across the skin surface, depositing a film of fluid on the skin. Commonly the dispenser is wiped across the skin between 4 and 10 strokes. Commonly from 0.2 to 0.5 g of the composition is deposited in each armpit per application.

The method of attaining an antiperspirant benefit described as the third aspect of the invention (vide supra) may involve direct or indirect topical application to the composition surface of the human body. In a related method, a composition comprising an antiperspirant salt prepared by drying an antiperspirant solution prepared according to the second aspect of the invention may be topically applied to the surface of the human body, directly or indirectly. In each of the methods described in this paragraph, the composition is preferably applied to the underarm regions of the human body.

EXAMPLES

In the following examples, all percentages are by weight, unless otherwise indicated.

The Chlorohydrol 50 solution was an aqueous solution comprising approximately 50% by weight of aluminium chlorohydrate (ACH) and was obtained from SummitReheis. We measured its Al content at 12.9% by weight. The ACH has an approximate general formula $Al_2(OH)_5Cl$ and an Al:Cl ratio of approximately 2:1.

The Reach 301 powder was approximately 100% ASCH and was obtained from SummitReheis. We measured its Al content at 24.1% by weight. The ASCH had an approximate general formula of $Al_2(OH)_{4.8}Cl_{1.2}$ and an Al:Cl ratio of approximately 1.67:1.

The Aloxicoll 31 L solution was an aqueous solution comprising approximately 50% by weight of ASCH and was obtained from BK Giulini GmbH. We measured its Al content at 11.9% by weight. The ASCH had an approximate general formula of $Al_2(OH)_{4.8}Cl_{1.2}$ and an Al:Cl ratio of approximately 1.67:1.

The anhydrous calcium chloride and glycine were ex Sigma-Aldrich.

A range of antiperspirant (AP) salt solutions (1-12) was prepared as follows.

Solution 1

30 parts of Chlorohydrol 50 solution was combined with 63.8 parts water at room temperature. The resulting solution had a Band III content of 15%.

Solution 2

15 parts of Reach 301 powder was dissolved in 78.9 parts water at room temperature. The resulting solution had a Band III content of 27%.

Solution 3

30 parts of Chlorohydrol 50 solution, 1.5 parts anhydrous calcium chloride and 4.7 parts glycine were combined with 57.6 parts water at room temperature. The resulting solution was heated at 85° C. for 18 hrs in a capped glass vessel and was then allowed to cool to ambient temperature. The resulting solution had a Band III content of 55%.

Solution 4

15 parts of Reach 301 powder, 1.5 parts anhydrous calcium chloride and 4.7 parts glycine were combined with 72.6 parts water at room temperature. The resulting solution was heated at 85° C. for 18 hrs in a capped glass vessel and was then allowed to cool to ambient temperature. The resulting solution had a Band III content of 62%.

Solution 5

7.5 parts of Reach 301 powder, 0.75 parts anhydrous calcium chloride and 2.35 parts glycine were combined with 83.2 parts water at room temperature. The resulting solution was heated at 85° C. for 18 hrs in a capped glass vessel and was then allowed to cool to ambient temperature. The resulting solution had a Band III content of 63%.

Solution 6

15 parts of Reach 301 powder, 0.9 parts anhydrous calcium chloride and 2.0 parts glycine were combined with 75.9 parts water at room temperature. The resulting solution was heated at 85° C. for 18 hrs in a capped glass vessel and was then allowed to cool to ambient temperature. The resulting solution had a Band III content of 42%.

Solution 7

5 parts of Reach 301 powder, 0.3 parts anhydrous calcium chloride, and 0.67 parts glycine were combined with 87.83 parts water at room temperature. The resulting solution was heated at 85° C. for 18 hrs in a capped glass vessel and was then allowed to cool to ambient temperature.

Solution 8

15 parts of Reach 301 powder, 1.5 parts anhydrous calcium chloride and 4.7 parts glycine were combined with 72.6 parts water at room temperature. The resulting solution was heated to 115° C. for 50 seconds and maintained at this temperature for a further 194 seconds in UHT processing equipment at a pressure of 3 to 7 Bar, and was then cooled over 56 seconds. The resulting solution had a Band III content of 52%.

Solution 9

30 parts of Reach 301 powder, 3.0 parts anhydrous calcium chloride and 9.4 parts glycine were combined with 57.6 parts water at room temperature. The resulting solution was heated at 85° C. for 18 hrs in a capped glass vessel. The resulting solution had a Band III content of 69%.

Solution 10

30 parts Aloxicoll 31 L, 0.9 parts anhydrous calcium chloride and 2.0 parts glycine were combined with 2.6 parts water at room temperature. The resulting solution was heated to 135° C. for 99 seconds and maintained at this temperature for 389 seconds in UHT processing equipment at a pressure of 3 to 7 Bar, and was then cooled, over 200 seconds. The resulting solution had a Band III content of 31%.

Solution 11

60 parts of Chlorohydrol 50 solution was combined with 40 parts water at room temperature.

Solution 12

30 parts of Reach 301 powder, 3.0 parts calcium chloride anhydrous (Sigma-Aldrich), 5.4 parts glycine (Sigma-Aldrich) were combined with 57.6 parts water at room temperature. The resulting solution was heated at 85° C. for 18 hrs in a capped glass vessel.

Each of solutions 1 to 8 was used in the preparation of an antiperspirant roll-on composition as indicated in Table 1. Each of solutions 9 and 10 was used in the preparation of antiperspirant roll-on compositions as indicated in Table 2. Each of solutions 11 and 12 was used in the preparation of an antiperspirant cream composition as indicated in Table 4.

The roll-on compositions of Table 1 were prepared at a 1.5 kg scale. The AP salt solution was placed in a large glass vessel. This was heated to 52° C. while stirring with a Silverson mixer (2 inch head, square mesh, high shear screen) at 1500 rpm. The Steareth 20 was then added to the AP salt solution and allowed to dissolve. In a separate vessel the sunflower seed oil and Steareth 2 were combined and heated to 65° C. with gently stirring. The stirring speed of the Silverson mixer on the main vessel was increased to 2500 rpm and the mixture of sunflower seed oil and Steareth 2 added over 9 minutes while maintaining the temperature at 52° C. The temperature was then reduced to 42° C. and the fragrance added. The Silverson speed was increased to 7500 rpm for 3 minutes and then the resulting emulsion mixture was dispensed into standard roll-on packs.

TABLE 1

Antiperspirant Roll-On Composition

| Component: | % w/w |
| --- | --- |
| AP salt Solution 1 to 8 | 93.8 |
| Steareth 20 (1) | 0.9 |
| Steareth 2 (2) | 2.3 |
| Sunflower seed oil (3) | 2.0 |
| Fragrance | 1.0 |

1. Volpol S20, ex Croda.
2. Volpol S2A, ex Croda.
3. Akosun, ex AAK Karlshmans.

The roll-on compositions of Table 2 were prepared in exactly the same way as those in Table 1, except that the AP salt solution was pre-diluted with additional water as indicated.

TABLE 2

| | % w/w Example: | |
| --- | --- | --- |
| Component: | 6 | 7 |
| AP salt Solution 9 | 50 | — |
| AP salt Solution 10 | — | 35.5 |
| Water | 43.8 | 58.3 |
| Steareth 20 (1) | 0.9 | 0.9 |
| Steareth 2 (2) | 2.3 | 2.3 |
| Sunflower Seed Oil (3) | 2.0 | 2.0 |
| Fragrance | 1.0 | 1.0 |

The roll-on compositions as described in the above two tables are summarised in Table 3, together with the "sweat weight reduction" (SWR) attained on use of each of the compositions.

TABLE 3

| Example | AP salt solution | AP sal (Approximate %) | Molar ratio Ca:Al | Molar ratio Glycine:Al | SWR (%) |
| --- | --- | --- | --- | --- | --- |
| A | 1 | 15 | 0 | 0 | 41 |
| B | 2 | 15 | 0 | 0 | 41 |
| C | 3 | 15 | 1:10.6 | 1:2.3 | 48 |
| 1 | 4 | 15 | 1:9.9 | 1:2.1 | 58 |
| 2 | 5 | 7.5 | 1:9.9 | 1:2.1 | 56 |
| 3 | 6 | 15 | 1:16.5 | 1:5.0 | 60 |
| 4 | 7 | 5 | 1:16.5 | 1:5.0 | 41 |
| 5 | 8 | 15 | 1:9.9 | 1:2.1 | 56 |
| 6 | 9 | 15 | 1:9.9 | 1:2.1 | 62 |
| 7 | 10 | 15 | 1:16.3 | 1:5.0 | 59 |

The SWR results were obtained using a test panel of 30 female volunteers. Test operators applied Comparative Example A (0.30 g) to one axilla and 0.30 g of non-antiperspirant deodorant body spray to the other axilla of each panellist. This was done once each day for three days. After the third application, panellists were requested not to wash under their arms for the following 24 hours.

24 hours after the third and final product application, the panellists were induced to sweat in a hot-room at 40° C. (±2° C.) and 40% (±5%) relative humidity, for 40 minutes. After this period, the panellists left the hot-room and their axillae were carefully wiped dry. Pre-weighed cotton pads were then applied to each axilla of each panellist and the panellists re-entered the hot-room for a further 20 minutes. Following this period, the pads were removed and re-weighed, enabling the weight of sweat generated to be calculated.

The sweat weight reduction (SWR) for each panellist was calculated as a percentage (% SWR) and the mean % SWR was calculated according to the method described by Murphy and Levine in "Analysis of Antiperspirant Efficacy Results", *J. Soc. Cosmetic Chemists*, 1991 (May), 42, 167-197.

For Comparative Examples B and C and Examples 1 to 7, the above procedure was repeated except that the product with which the test sample was compared was Comparative Example A. For ease of reference, each SWR figure for these latter products is a calculation based upon the 41% result for Comparative Example 1 and the further SWR (or not) obtained on comparison of said product with Comparative Example 1. For example, Example 2 had an SWR relative to Comparative Example A of 25%. Since Comparative Example A stopped all bar 59% of sweat production, the SWR figure for Example 2 is 41+(59×0.25)=56%.

Comparative example A, a BAC composition lacking calcium chloride and glycine, gave a SWR of 41%. Comparative example B, an ASCH composition also lacking calcium chloride and glycine, also gave a SWR of 41%. Comparative example B, a BAC composition having calcium chloride and glycine, gave a somewhat better SWR of 48%.

Example 1, an ASCH composition having calcium chloride and glycine, gave a SWR of 59%, a significantly better performance than Comparative examples A, B, or C. Surprisingly, Example 2, having only half the AP salt level of Example 1, gave a SWR of 56%.

Example 1 was tested again after the sample had been stored for 12 weeks at 45° C. The SWR on this latter occasion was 62%, not significantly different to the earlier result, illustrating the excellent stability of examples according to the invention.

Examples 3 and 4 were prepared using much lower ratios of calcium to aluminium and glycine to aluminium compared with Examples 1 and 2. Nevertheless, Example 3 gave an excellent SWR of 60% and Example 4 was able to match the performance of Comparative examples A and B despite only having a third the level of AP salt present.

The cream compositions indicated in Table 4 were prepared using Solutions 11 and 12 (vide supra) at 1.5 kg scale. The water and glycerol were combined and heated to 80° C. in a main vessel with gentle stirring (low speed scraper blade mixer). In a second vessel the glyceryl stearate, liquid petrolatum, cetearyl alcohol and Polawax GP200 were combined and heated 80° C. with gentle stirring (magnetic stirrer bar). While maintaining the temperature at 80° C., the contents of the second vessel were then added slowly to the main vessel. The speed of the scraper blade mixer was adjusted throughout the addition to ensure good mixing at all times. While maintaining temperature and mixing, the titanium dioxide was then added and dispersed. The temperature was reduced to 50° C. and the AP salt solution added. The temperature was reduced to 40° C. and the fragrance added. Once fully mixed the formulation was placed in a suitable dispenser.

TABLE 4

| Component: | % w/w |
|---|---|
| AP salt solution 11 to 12 | 50 |
| Water | 32.6 |
| Glyceryl Stearate | 7.5 |
| Liquid Petrolatum (4) | 1.0 |
| Glycerol (5) | 1.5 |
| Titanium Dioxide (6) | 0.2 |
| Cetearyl alcohol (7) | 1.0 |
| Cetearyl alcohol, PEG-20 Stearate (8) | 5.0 |
| Fragrance | 1.2 |

4. Liquid petrolatum (Blanol, ex Evonik Degussa).
5. Glycerol (Pricerine 9091, ex Croda).
6. Titanium dioxide (Tiona AG, ex Aston Chemicals).
7. Cetearyl alcohol (Laurex CS, ex Huntsman).
8. Polawax GP200, ex Croda.

The cream compositions as described in the above table are summarised in Table 5, together with the "sweat weight reduction" (SWR) attained on use of each of the compositions.

TABLE 5

| Example | AP salt solution | AP salt in composition (Approximate %) | Molar ratio Ca:Al | Molar ratio Glycine:Al | SWR (%) |
|---|---|---|---|---|---|
| D | 11 | 15 | 0 | 0 | 38 |
| 8 | 12 | 15 | 1:12.4 | 1:4.7 | 61 |

The SWR results were obtained using the same method as described immediately below Table 3, Comparative Example D and Example 8 each being compared with a non-antiperspirant deodorant body spray. Example 8 gave a significantly better SWR figure than Comparative Example D.

In a further series of experiments, antiperspirant salt solutions analogous to Solution 4 as described above were prepared. The preparatory procedure for Solution 4R was exactly the same as for Solution 4. For Solution 4LA, the procedure was exactly the same except that the 4.7 parts glycine was replaced by 4.7 parts lactic acid. For Solution 4GA the procedure was exactly the same except that the 4.7 parts glycine was replaced by 4.7 parts glycolic acid. Following preparation, the solutions were analysed using SEC by a method based upon that described in U.S. Pat. No. 4,359,456 by Gosling. The results are indicated below.

TABLE 6

| Solution | Band III content |
|---|---|
| 4R | 70% |
| 4LA | 27% |
| 4GA | 23% |

The results indicate that the amino acid glycine is more effective at activating the ASCH than either of the hydroxy acids.

The invention claimed is:

1. An aqueous composition comprising an aluminium sesquichlorohydrate salt, water soluble calcium salt, and amino acid, wherein the aluminium sesquichlorohydrate salt is of formula $Al_2(OH)_{4.7}Cl_{1.3}$ to $Al_2(OH)_{4.9}Cl_{1.1}$ and the molar ratio of calcium to aluminium is from 1:20 to 1:5 and the molar ratio of amino acid to aluminium is from 1:5 to 1:1, wherein the composition is an oil-in-water emulsion comprising an emulsifier, and wherein the emulsion has a continuous phase that is greater than 50% by weight water.

2. The composition according to claim 1, wherein the water soluble calcium salt is calcium chloride and the amino acid is glycine.

3. The composition according to claim 1, wherein the aluminium sesquichlorohydrate salt has a Band III content measured by SEC of greater than 40% relative to the total integrated area in all of the regions corresponding to aluminium species.

4. The composition according to claim 1, wherein the aluminium sesquichlorohydrate salt has a Band III content measured by SEC of greater than 50% relative to the total integrated area in all of regions corresponding to aluminium species.

5. The composition according to claim 1, wherein molar ratio of calcium to aluminium is from 1:15 to 1:5 and the molar ratio of amino acid to aluminium is from 1:4 to 1:1.

6. The composition according to claim 5, wherein molar ratio of calcium to aluminium is from 1:10 to 1:5 and the molar ratio of amino acid to aluminium is from 1:3 to 1:1.

7. A method of attaining an antiperspirant benefit comprising the topical application to the surface of the human body of an antiperspirant composition according to claim 1.

* * * * *